US005679333A

United States Patent [19]
Dunphy

[11] Patent Number: 5,679,333
[45] Date of Patent: Oct. 21, 1997

[54] FORMALDEHYDE-FREE TISSUE PRESERVATIVE COMPOSITIONS

[76] Inventor: Brian William Dunphy, 235 Castletown Rd.,, Timonium, Md. 21093

[21] Appl. No.: 738,048

[22] Filed: Oct. 25, 1996

[51] Int. Cl.$^6$ ................................ A61L 9/00; A01N 1/00
[52] U.S. Cl. ................... 424/75; 422/5; 422/28; 422/29; 422/36
[58] Field of Search ................... 424/75; 422/5, 422/28, 29, 36

[56] References Cited

U.S. PATENT DOCUMENTS 4,278,715  7/1981  Romero-Sierra et al. ............ 428/22
5,405,606  4/1995  Campbell et al. ..................... 424/75
5,607,668  3/1997  Campbell et al. ..................... 424/75

*Primary Examiner*—Thurman K. Page
*Assistant Examiner*—Kathryne E. Shelborne
*Attorney, Agent, or Firm*—Rothwell, Figg, Ernst & Kurz

[57] ABSTRACT

Formaldehyde-free tissue preservative compositions are useful in the fields of mortuary science and histology. The compositions disinfect and preserve animal (including human) tissues and remains, yet avoid the use of formaldehyde and formalin—potentially hazardous materials that are undergoing increasing regulatory review. A trio of compositions for use in embalming human bodies is disclosed, as is a composition for use in histological preservation.

21 Claims, No Drawings

FORMALDEHYDE-FREE TISSUE PRESERVATIVE COMPOSITIONS

BACKGROUND OF THE INVENTION

1. Technical Field

The present invention relates to the field of preservation of human tissue in the mortuary science and the anatomic pathology (histology) disciplines. More particularly, the invention relates to formaldehyde-free compositions for use in that field of science.

2. Description of the Background Art

Since the turn of the century practitioners of mortuary science have placed near total reliance on solutions containing formaldehyde in high concentration to preserve and disinfect human remains. During the same time period histologists and anatomic pathologists have likewise placed reliance upon solutions containing formaldehyde, albeit in much lower concentration, to preserve human tissue for examination. While formaldehyde is an excellent tissue preservative in that it disinfects and preserves human tissue (primarily by cross-linking proteins), is readily available and is generally inexpensive to use, it does, however, subject the user to significant health risks.

Within the past two decades the use of formaldehyde in the workplace has become subject to regulation because formaldehyde has been declared a probable human carcinogen. In light of such findings, governmental regulatory authorities (including the U.S. Department of Labor, Occupational Safety and Health Administration) placed increasingly stringent limits upon workplace formaldehyde vapor exposure.

Workers in mortuary science settings—including embalmers, handlers of human remains and students in a variety of medically-related fields—are routinely exposed to high concentrations of formaldehyde vapors. Whereas in the anatomic pathology laboratory where pathologists, histologists, researchers and students are exposed to formaldehyde-containing solutions (formalins) of lower concentration (3.5% to 4% in water), mortuary science workers are constantly exposed to vaporous formaldehyde in high concentration, upwards of 25% to near saturation in water (40%). Repeated exposure to formaldehyde vapors has been associated with carcinogenesis (cancer formation) in laboratory animals (epitheliomas, nasopharyngeal cancer), and a human pulmonary pathology condition ("embalmer's lung") has been described, owing wholly or in part to environmental formaldehyde vapor exposure.

Awareness of the dangers associated with repetitive formaldehyde vapor exposure has provided a stimulus for the search for alternatives to formaldehyde for use in mortuary science and anatomic pathology settings. Such an alternative must satisfy a triad of equally important requirements: efficacy, economy and safety. Accordingly, there is a great need in the mortuary industry, and related medical and scientific fields, for low-cost formaldehyde-free tissue preservative compositions.

SUMMARY OF THE INVENTION

Satisfying the need to develop safe, effective and economical alternatives to formaldehyde-containing solutions for use in mortuary science and anatomic pathology settings, the present invention provides solutions to be used in combination with one another or individually for embalming animal remains (including human remains) and related tasks, and for use as a fixative of animal (including human) tissue. All of the solutions share the common attribute of not containing formaldehyde in their composition.

In one aspect, the present invention provides a formaldehyde-free tissue preservative comprising an aqueous solution of ethanol, ethanedial, a long-chain polymer and a polar aprotic solvent. In some embodiments of the invention this tissue preservative composition is optimized for use as an arterial injection fluid for use in preserving animal (especially but not exclusively human) bodies (remains), for example in the mortuary science industry. In other embodiments, the tissue preservative composition is optimized for use in the histology field to preserve tissue samples.

In another aspect, the present invention relates to a method for preserving human bodies (as well as remains of other animals), comprising injecting into the circulatory system of the body a tissue preservative composition as described above. The components of the composition serve to disinfect and preserve the body in accordance with the desires of those practicing in the mortuary science field.

In yet another aspect, the invention provides formaldehyde-free compositions (pre-injection compositions) which function to clear and cleanse the circulatory system in preparation for the administration of the tissue preservative composition. These compositions comprise aqueous solutions of ethanedial, a polar aprotic solvent, a proteolytic enzyme, a surfactant, an anti-microbial agent and, optionally, a chelating agent.

Additionally, the invention provides a formaldehyde-free body cavity fluid for use in the embalming process, which comprises an aqueous solution of ethanol, an organic acid, a polar aprotic solvent, ethanedial and Bisphenol A.

DETAILED DESCRIPTION OF THE PREFERRED EMBODIMENTS

The present invention provides, in one aspect, formaldehyde-free compositions (solutions) for use in the mortuary science setting to treat and preserve animal remains including human bodies. The use of the compositions in the process of embalming human bodies is particularly preferred. In that context, the invention provides a pre-injection fluid, a tissue preservative for arterial injection and a body cavity fluid. The invention also provides a non-formaldehyde tissue fixative solution for use in the field of histology. All compositions preferably are provided as aqueous solutions in distilled or de-ionized water.

Formaldehyde-Free Mortuary Science Embalming Fluids 1) pre-Injection (and Co-Injection) Fluid The term "pre-injection" fluid is used herein to denote a composition that typically is administered into the circulatory system of a human body, as an initial part of the embalming process, prior to the injection of the major tissue preservative composition. The major role of the pre-injection fluid is to clear clots and other obstructions from the circulatory system (primarily the vascular system), although the pre-injection fluid can have some tissue preservation and disinfection properties. Alternatively, this composition can be mixed with and administered at the same time as the major tissue preservative composition, whereupon this composition is more accurately referred to as a "co-injection" fluid.

The pre-injection fluid of the present invention is an aqueous solution containing, in preferred embodiments, a biodegradable anionic or nonionic surfactant (e.g. a sodium alkyl sulfonate-based detergent), a proteolytic enzyme (protease) preferably of vegetative origin, a chelating agent (e.g. ethylenediamine tetraacetic acid (EDTA) as a disodium salt)); an antimicrobial agent (e.g. a powerful quaternary ammonium salt such as 1-hexadecylpyridinium chloride), a polar aprotic solvent (e.g. dimethyl sulfoxide (DMSO)), and a stable aldehyde, ethanedial.

The protease enzyme is particularly useful for aiding the removal of fibrin deposits and clots within the vascular system. Although a variety of commercially-available protease enzymes may be used, Type II, Fungal, Crude, derived from *Aspergillus oryzae*, is a preferred protease enzyme. Type XXIII, from *Aspergillus oryzae* activity, may also be used. Although this enzyme has higher proteolytic activity, its cost is significantly greater than that of Type II, Fungal, Crude.

The pre-injection fluid desirably has an acidic pH. Preferred compositions have a pH of about 4.

Use of the pre-injection fluid as part of the process of embalming human bodies provides several functions. In addition to conditioning water used to physically flush vascular lumae and tissue interstices by chelating divalent cations found in some tap waters, the fluid helps dissolve intravascular clots and fibrin deposits and residues, loosens athero-sclerotic deposits (plaques) and cleanses the vascular system to create a patent circuit for the subsequent injection of arterial injection (tissue preservative) fluid. Although not wishing to be bound by any particular theory, it is believed that dimethyl sulfoxide mediates the flow of the antimicrobial agent and ethanedial into cells from tissue interstitial spaces such that disinfection is commenced, and a minimal degree of tissue hardening is begun through the crosslinking of cellular membrane proteins by ethanedial. Residual fluid remaining in the tissue interstices following evacuation of the pre-injection fluid serves to prevent growth and propagation of microorganisms. The flushing action of the pre-injection fluid further helps remove tissue metabolic wastes, as well as exogenous substances such as therapeutic drugs, drug metabolites and chemotherapeutic agents.

When used as a pre-injection fluid (that is, prior to the application of tissue preservative), the fluid is diluted in tap water to 1:8 strength and injected into the vascular system to commence flushing activity. Alternatively, the fluid can be used as a "co-injection fluid" by co-administering it simultaneously with, rather than before, the tissue preservative. In this manner a several-ounce quantity of the stock solution is added to stock arterial injection fluid prior to dilution with tap water for injection. The ratio of co-injection fluid to arterial fluid can vary and can be selected by the embalmer, but it is suggested the ratio is 1:3 prior to dilution of a pint of the blend to make a gallon of injectable blended fluid.

2) Arterial Injection (Tissue preservative) Fluid

The arterial injection fluid of the present invention functions primarily as a tissue preservative, disinfecting and preserving body tissues, including cross-linking proteins, without the use of formaldehyde. The arterial injection fluid is an aqueous solution composed of, in preferred embodiments, an alcohol (ethanol), a humectant (e.g. 1,2-ethanediol (ethylene glycol), a polymer of ethylene glycol (polyethylene glycol or "PEG"), an organic acid, preferably a mild acid, such as ethanoic acid (acetic acid), a polar aprotic solvent (e.g. dimethyl sulfoxide (DMSO)), an antimicrobial agent, such as the powerful quaternary ammonium salt, 1-hexadecylpyridinium chloride, a chelating agent (e.g. a salt of ethylenediaminetetraacetic acid (EDTA)), and a stable aldehyde, ethanedial. A colorizing agent such as tetrabromofluorescein (eosin Y), and other ingredients commonly employed in embalming fluids, may be included.

The polyethylene glycol polymer preferably has an average molecular weight between about 7000 and 9000, and most preferably has an average molecular weight of 8000. Commercially-available polyethylene glycol preparations typically contain a distribution of polymer chains of varying lengths and hence molecular weights; thus, referring to an "average" molecular weight is common. Polyethylene glycol polymers of substantially lower molecular weights (e.g. below 1000) generally are not "rigid" or "solid" enough to provide the desired physical properties, and polymers of substantially higher molecular weights typically are more expensive than, but do not function substantially better than, polymers in the commercially-preferred 7000–9000 molecular weight range. The arterial injection fluid preferably has a relatively acidic pH, with preferred compositions having a pH of about 4.

The functions of the arterial injection fluid are those of preserving human tissue remains by arresting the natural autolytic process; of preventing or retarding the growth and propagation of microorganisms in situ; and of stabilizing tissue by crosslinking proteins, thereby causing the tissues to harden or "leatherize" as is known in the mortuary science.

Although not wishing to be bound by any particular theory, the process by which the arterial injection fluid preserves, disinfects and stabilizes human tissue remains in situ is not a static process, but rather a dynamic of events. It is believed that the process occurs as follows:

The arterial fluid is injected into the body through a suitably patent large blood vessel. The fluid under mild positive pressure is distributed throughout body tissues after flow through continually subdivided blood vessels to the interstitial spaces about the cells. The fluid enters cells by diffusion, and it is believed the action of a minute amount of polar aprotic solvent (preferably DMSO) helps mediate the diffuse flow of the fluid into cells by increasing cellular membrane permeability. Once inside the cells, ethanol begins to denature intracellular proteins by dehydration and coagulation. This is an important first step in the preservation process, for upon denaturation of intracellular proteins the natural autolytic (decaying) process is arrested. As intracellular proteins dehydrate there is a tendency of the cells to shrink due to loss of intracellular fluids. A weak concentration of organic acid in the fluid helps reverse the shrinkage of the cells by drawing fluids from the outlying spaces as it enters the cells (equilibration). The entrance of high molecular weight polymerized ethylene glycol (polyethylene glycol) tends to fill vacant intracellular spaces, giving rigidity to the cellular structure. Ethylene glycol serves as a humectant, serving to draw moisture into cells to complete the equilibration of cellular osmotic pressure. While ethanol in the fluid contributes to bacteriostasis, true bacteriocidal activity is conferred to the fluid via the presence of an antimicrobial agent, preferably in the form of a powerful quaternary ammonium salt, 1-hexadecylpyridinium chloride, which in the working solution is present in a concentration of 1:15000—potent enough to kill a broad range of microorganisms including most common bacterial pathogens encountered in vegetative form in human remains. In addition, polyethylene glycol is an effective inhibitor of molds. Stabilization of tissues is completed by the action of ethanedial. Ethanedial is believed to crosslink cellular membrane proteins by bonding aldehydic functional groups to amino acids' functional groups. Crosslinkage of tissues results in leatherization of tissues, imparting a variable degree of stiffening or hardening of tissues. Lastly, a chelating agent, ethylenediaminetetraacetic acid, sequesters divalent cations present in some tap waters which may cause undesirable performance of embalming fluids. The chelating agent also removes divalent cations which are important co-factors necessary for bacterial enzymatic activity, further acting as a secondary bacteriostatic agent. As an option, a dye, eosin Y, may be added to the fluid as a colorizing agent, and as an aid in tracking the flow of the fluid through the body.

In its preferred concentration, the arterial injection fluid is designed to be diluted 1:8 (16 oz. fluid plus 112 oz. tap water to measure one gallon working solution) prior to injection.

3) Body Cavity Fluid

The body cavity fluid of the present invention is an aqueous solution of ethanol, an organic acid, (e.g. ethanoic acid), a polar aprotic solvent (e.g. DMSO), an antimicrobial agent effective against spore-forming bacteria (e.g. 4-4'-isopropylidenediphenol (Bisphenol A)) and ethanedial. The body cavity fluid functions to disinfect evacuated body cavities and to preserve removed gross organic tissue returned to the body for interment.

During the embalming of human remains, certain body cavities such as the peritoneal and thoracic cavities are evacuated of the natural fluids which fill these spaces. Removal of the cavity fluids is necessary to deny microorganisms a rich media in which to grow. Once evacuated of natural body fluids the cavities must be filled with a suitable fluid to prevent the growth and propagation of microorganisms.

Upon death, normally saprophytic bacteria, especially those capable of endospore formation, may migrate out of the gut and into the peritoneal cavity where they begin to digest tissue with deleterious effect. Of particular concern to embalmers is the process of purging, where gas liberated from tissue putrification infiltrates tissue membranes causing discoloration of the skin and swelling. The bacteria most usually associated with the formation of ptomaines (putrescine, cadaverine) are those of the genus Clostridium. These bacteria possess decarboxylase enzymes which break down amino acids, forming ptomaines and carbon dioxide (gas). The Clostridia bacteria are particularly capable of endospore formation, making them difficult to kill with many bacteriocidal agents. Thus, the body cavity fluid of the present invention contains sporicidal agents (i.e., antimicrobial agents effective against spore-forming bacteria).

Organs sometimes are removed from the body at autopsy for examination. After examination the organs are returned for placement into the body at interment. It is necessary that a powerful preservative containing a sporicide be used to preserve and disinfect these organs. Returned organs are placed in a suitable sealed plastic bag container which is placed in the chest cavity and the chest is sewn closed tightly. Clearly, the prevention of tissue putrification and gas production is critical in this environment.

Using the described body cavity fluid, disinfection of body cavity spaces is accomplished by the dehydrating action of ethanol present in a strength of 70%, a level of ethanol concentration incompatible with life of vegetative bacteria but not of endospore bacteria. The fluid contains an ingredient specifically included as a sporicide, Bisphenol A, which has been demonstrated to kill spore forms of the bacteria, *Clostridium perfringes*, the bacterium most closely associated with gas production and purging following putrification of tissues. An acid is present in the cavity type fluid to render the pH of the fluid decidedly acidic; *Clostridium perfringes* requires a neutral or slightly alkaline pH media for growth. Preferred compositions have a pH of about 2. Dimethyl sulfoxide serves to mediate fluid movement across cellular membranes, and ethanedial completes tissue stabilization by crosslinking proteins to "leatherize" the tissues.

The preferred composition of the body cavity embalming fluid is designed for use undiluted, to be injected directly into evacuated body cavities, or to be poured directly into containers of human gross organs prior to sealing.

4) Formaldehyde-Free Tissue Fixation Fluid

Another preferred embodiment of the tissue preservative composition of the present invention is provided as a tissue fixative for use in the histology field. This tissue fixative is an aqueous solution of ethanol, humectant (e.g. 1,2-ethanediol (ethylene glycol)), a long-chain polymer such as PEG of molecular weight 7000 to 9000, an organic acid (e.g. acetic acid), a polar aprotic solvent (e.g. dimethyl sulfoxide) and ethanedial. The solution typically has a relatively acidic pH, but may be buffered to a substantially neutral pH (e.g. within the range of about 6.8 to about 7.8). The addition of approximately 4 grams acid sodium phosphate monohydrate and 6.5 grams disodium phosphate (anhydrous) per liter of solution generally is effective to buffer the solution within this preferred pH range.

The purpose of the tissue fixative is to prevent autolysis of tissue removed from the body such that the tissue most closely resembles that as it exists in its natural in situ state. Tissue samples which are taken from the body during surgery, in biopsy or at autopsy are processed and stained for microscopic examination. It is of paramount important that tissue become fixed or rended free of autolysis (self-destruction) immediately after collection. In tissue analysis a fixative must be uniformly effective in penetrating tissue from the outside inward such that all cells are rendered autolytic.

The mode of action of tissue fixation is similar to that encountered in arterial fluid embalming with a major distinction between the two processes. In embalming, arterial fluid is situated for diffusion into individual cells from interstitial spaces under mild positive pressure. In tissue fixation the fixative solution must enter cells passively through penetration of tissue thicknesses without outside pressure. The latter is a slow process requiring several hours to days to accomplish, and is a function of tissue thickness and composition. Simple epithelial tissue fixes rapidly compare to tissues high in fat content such as breast, colon and brain. The process of fixation may be accelerated with the use of microwave energy which heats the tissues.

It is believed that the described formaldehyde-free tissue fixative is a dual pathway fixative, accomplishing its function by both intracellular as well as extracellular fixation. This is similar to the action of the arterial injection fluid of the present invention. It is believed that dimethyl sulfoxide in minute concentration mediates the passive diffusion of ethanol across cellular membranes such that intracellular proteins are fixed by dehydration and coagulation. To counter loss of intracellular fluids, ethanoic acid causes an influx of both ethylene glycol, a humectant, and its high molecular weight polymer, polyethylene glycol, which firms intracellular spaces vacated by tissue fluid loss. Extracellular fixation is accomplished through the crosslinking of cell membrane amino acid functional groups by the aldehydic groups of ethanedial.

EXAMPLE 1

The following table describes preferred embodiments of a pre-injection (co-injection) composition of the present invention. The table presents a description of a particularly preferred composition, as well as a preferred range for each ingredient.

| Ingredient | Preferred Composition | Range |
|---|---|---|
| Sodium Alkyl Sulfonate | 3.0% w/v | 2.0–4.0% |
| Ethanedial | 14.0% v/v | 12.0–16.0% |
| 1-Hexadecylpyridinium Chloride | 0.06% w/v | 0.05–0.07% |
| EDTA | 0.08% w/v | 0.06–0.10% |
| Dimethyl Sulfoxide | 0.0275% v/v | 0.025–0.03% |
| Protease Enzyme | 0.03% w/v | 0.02–0.04% |
| Water | 82.8% v/v | 79.8–85.8% |

EXAMPLE 2

The following table describes preferred embodiments of an injectable tissue preservative composition of the present invention, designed for injection into the circulatory system of a human body as part of the embalming process. The table presents a description of a particularly preferred composition, as well as a preferred range for each ingredient. All amounts are expressed as percent by volume or by weight as set forth in Example 1.

| Ingredient | Preferred Composition | Range |
|---|---|---|
| Ethanedial | 28.0% v/v | 24.0–32.0% |
| Ethanol | 15.0% v/v | 14.0–16.0% |
| Polyethylene Glycol | 2.5% w/v | 2.0–3.0% |
| Ethylene Glycol | 0.3% v/v | 0.2–0.4% |
| Ethanoic Acid | 0.5% v/v | 0.4–0.6% |
| 1-Hexadecylpyridinium Chloride | 0.06% w/v | 0.05–0.07% |
| Dimethyl Sulfoxide | 0.0275% v/v | 0.025–0.030% |
| EDTA | 0.08% w/v | 0.06–0.10% |
| Water | 53.5% v/v | 47.8–59.3% |

EXAMPLE 3

The following table describes preferred embodiments of a body cavity fluid for use in the embalming process, according to the present invention. The table presents a description of a particularly preferred composition, as well as a preferred range for each ingredient. All amounts are expressed as percent by volume or by weight as set forth in Examples 1 and 2.

| Ingredient | Preferred Composition | Range |
|---|---|---|
| Ethanol | 70.0% v/v | 69.0–71.0% |
| Ethanedial | 5.0% v/v | 4.0–6.0% |
| Ethanoic Acid | 2.0% v/v | 1.0–3.0% |
| Dimethyl Sulfoxide | 0.0275% v/v | 0.025–0.03% |
| Bisphenol A | 0.5% w/v | 0.4–0.6% |
| Water | 22.5% v/v | 19.4–25.6% |

EXAMPLE 4

The following table describes preferred embodiments of a tissue fixative composition of the present invention, designed for use in preserving tissue samples for histological study and evaluation. The table presents a description of a particularly preferred composition, as well as a preferred range for each ingredient. All amounts are expressed as percent by volume or by weight as set forth in Examples 1–3.

| Ingredient | Preferred Composition | Range |
|---|---|---|
| Ethanedial | 3.75% | 3.5–4.0% |
| Ethanol | 20.0% | 15.0–25.0% |
| Polyethylene Glycol | 2.0% | 1.5–2.5% |
| Ethylene Glycol | 0.75% | 0.5–1.0% |
| Ethanoic Acid | 0.75% | 0.5–1.0% |
| Dimethyl Sulfoxide | 0.0275% | 0.025–0.030% |
| Water | 72.7% | 66.5–79.0% |

Although the present invention has been described in connection with certain preferred embodiments and specific compositions and ingredients, it is not so limited. Variations and modifications within the scope of the claims will be apparent to those knowledgeable in the mortuary science and tissue preservation fields and technologies.

I claim:

1. A formaldehyde-free tissue preservative comprising an aqueous solution of ethanol, ethanedial, a polymer and a polar aprotic solvent.

2. The tissue preservative according to claim 1, wherein said polymer is polyethylene glycol having a molecular weight of from about 7,000 to about 9,000.

3. The tissue preservative according to claim 1, wherein said polar aprotic solvent is DMSO.

4. The tissue preservative according to claim 1, further comprising a humectant.

5. The tissue preservative according to claim 4, wherein said humectant is 1,2-ethanediol.

6. The tissue preservative according to claim 1, further comprising an antimicrobial agent.

7. The tissue preservative according to claim 6, wherein said antimicrobial agent is 1-hexadecylpyridinium chloride.

8. The tissue preservative according to claim 1, further comprising a chelating agent.

9. The tissue preservative according to claim 8, wherein said chelating agent is EDTA or a salt thereof.

10. A formaldehyde-free tissue preservative composition, comprising an aqueous solution containing ethanol, ethanedial, a humectant, polyethylene glycol, an acid, a polar aprotic solvent and a chelating agent.

11. The tissue preservative according to claim 10, wherein the humectant is 1,2-ethanediol.

12. The tissue preservative according to claim 10, wherein the chelating agent is EDTA or a salt thereof.

13. The tissue preservative according to claim 10, wherein the acid is ethanoic acid.

14. A method of embalming a human body, comprising administering into the body a formaldehyde-free tissue preservative comprising an aqueous solution of ethanol, ethanedial, a polymer and a polar aprotic solvent.

15. A method of embalming a human body, comprising administering into the body a formaldehyde-free tissue preservative composition comprising an aqueous solution containing ethanol, ethanedial, a humectant, polyethylene glycol, an acid, a polar aprotic solvent and a chelating agent.

16. A method of embalming a human body, comprising:

(a) administering into the circulatory system of the body a formaldehyde-free pre-injection composition comprising an aqueous solution containing a surfactant, a proteolytic enzyme, an anti-microbial agent, a polar aprotic solvent and ethanedial; and (b) administering into the circulatory system of the body a tissue preservative composition comprising an aqueous solution of ethanol, ethanedial, a polymer and a polar aprotic solvent.

17. The method of embalming a human body according to claim 16, further comprising administering into the peritoneal and/or thoracic cavity of the body a formaldehyde-free body cavity preservation composition comprising an aqueous solution of ethanol, an acid, a polar aprotic solvent, an antimicrobial agent effective against spore-forming bacteria and ethanedial.

18. The method of embalming a human body according to claim 16, wherein said steps (a) and (b) are carried out sequentially.

19. The method of embalming a human body according to claim 16, wherein said steps (a) and (b) are carried out simultaneously.

20. The method of embalming a human body according to claim 16, wherein said tissue preservative composition comprises an aqueous solution containing ethanol, ethanedial, a humectant, polyethylene glycol, an acid, a polar aprotic solvent and a chelating agent.

21. The method according to claim 20, wherein said humectant is 1,2-ethanediol, said polar aprotic solvent is DMSO and said chelating agent is EDTA or a salt thereof.

* * * * *